United States Patent [19]

Ahrens et al.

[11] 3,962,453
[45] June 8, 1976

[54] NOVEL PYRAZOLYLOXYACETIC ACID DERIVATIVES AND PROCESS FOR THE PREPARATION THEREOF

[75] Inventors: Hans Ahrens; Helmut Biere; Clemens Rufer; Eberhard Schröder; Henning Koch, all of Berlin, Germany

[73] Assignee: Schering Aktiengesellschaft, Berlin & Bergkamen, Germany

[22] Filed: Sept. 12, 1974

[21] Appl. No.: 505,208

[30] Foreign Application Priority Data
Sept. 14, 1973  Germany............................ 2347015

[52] U.S. Cl................................ 424/273; 260/310 R
[51] Int. Cl.[2].............. A61K 31/415; C07D 231/18
[58] Field of Search................. 260/310 R; 424/273

[56] References Cited
FOREIGN PATENTS OR APPLICATIONS
34,517  10/1965  Finland........................... 260/310 R

*Primary Examiner*—Donald B. Moyer
*Attorney, Agent, or Firm*—Millen, Raptes & White

[57] ABSTRACT

Compounds of the formula

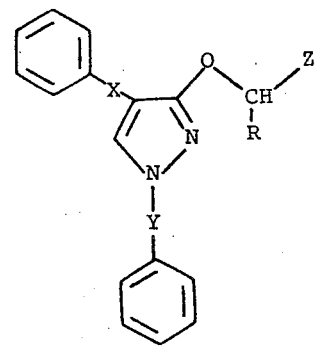

wherein X and Y each are a bond or methylene, R is H or lower-alkyl and Z is a carboxyl, amide, nitrile or alkoxycarbonyl of 1–6 carbon atoms in the alkoxy group and the corresponding compounds bearing 1–2 halogen, lower-alkyl or lower-alkoxy groups on one or both benzene rings and, when Z is carboxyl, salts thereof with physiologically acceptable bases, possess anti-inflammatory and antipyretic activities.

40 Claims, No Drawings

NOVEL PYRAZOLYLOXYACETIC ACID DERIVATIVES AND PROCESS FOR THE PREPARATION THEREOF

BACKGROUND OF THE INVENTION

This invention relates to novel pyrazolyloxyacetic acid derivatives and to a process for the preparation thereof.

2,4-Diaryl-3-pyrazoline-5-ones are known in the literature [M.J. Kornet et al., *J. Heterocycl. Chem.* 8, 999 (1971)] without any disclosure relative to the pharmacological activity of such compounds.

It has now been found that, by the alkylation of these and other compounds closely related thereto structurally, pyrazolyloxyacetic acid derivatives are obtained which possess useful pharmacological activity.

SUMMARY OF THE INVENTION

In a composition aspect, this invention relates to compounds of general Formula I

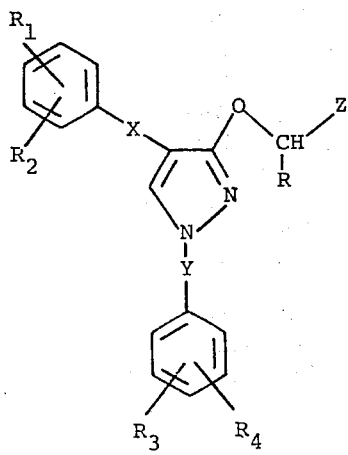

wherein R is a hydrogen atom or alkyl of 1–4 carbon atoms; $R_1$, $R_2$, $R_3$ and $R_4$, which can be alike or different, each are a hydrogen atom, a halogen atom, alkyl of 1–4 carbon atoms or alkoxy of 1–4 carbon atoms; X and Y, which can be alike or different, each are a direct bond joining the phenyl group to the pyrazolyl group or a methylene group, and Z is a carboxyl, amide, nitrile or alkoxycarbonyl group of 1–6 carbon atoms in the alkoxy group and, when Z is a carboxyl group, salts thereof with physiologically acceptable bases.

In another composition aspect, this invention relates to pharmaceutical compositions comprising a compound of Formula I.

In a process aspect, this invention relates to a process for the production of such compounds.

DETAILED DISCUSSION

Preferred compounds of Formula I include those wherein:

a. Z is carboxyl or alkoxycarbonyl of 1–6 carbon atoms in the alkoxy group, e.g., methoxycarbonyl, ethoxycarbonyl, as well as propoxycarbonyl and t-butoxycarbonyl;

b. R is a hydrogen atom, especially those of (a);

c. at least one and preferably both of X and Y are bonds, especially those of (a) and (b);

d. $R_1$, $R_2$, $R_3$ and $R_4$ each are H, Cl, $CH_3$ or $OCH_3$, especially those of (a), (b) and (c);

e. at least one and preferably at least two of $R_1$, $R_2$, $R_3$ and $R_4$ are hydrogen atoms, especially those of (a), (b), (c) and (d); and f. Z is carboxyl and the compound is in the form of an alkali metal or an amine salt, especially those of (b), (c), (d) and (e).

In addition to the compounds of the Examples hereinafter, other examples of the compounds of this invention are (1,4-diphenyl-3-pyrazolyloxy)-acetonitrile and (1,4-diphenyl-3-pyrazolyloxy)-acetamide.

Examples of physiologically acceptable bases are water soluble basic metallic salts, including hydroxides and carbonates, e.g., of the alkali metals, including sodium and lithium, and of the alkaline earth metals, including calcium and magnesium, and amines, preferably N-methylglucamine, N,N-dimethylglucamine, ethanolamine, diethanolamine and morpholine and other primary, secondary and tertiary aliphatic amines.

According to the process of this invention, the compounds of general Formula I are prepared by reacting a compound of general Formula II

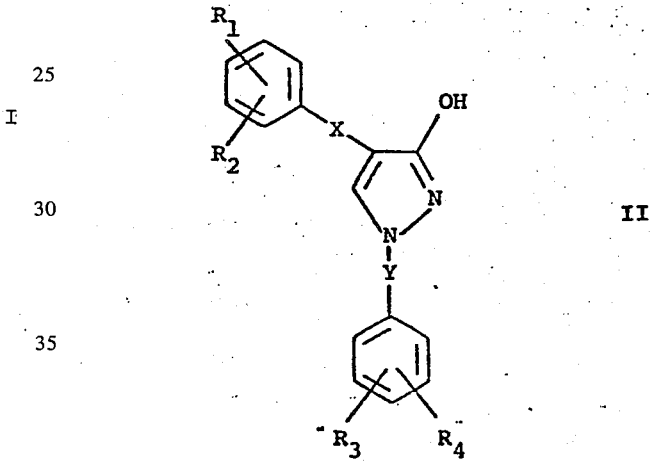

wherein X, Y, $R_1$, $R_2$, $R_3$ and $R_4$ have the values given above in the presence of a basic catalyst, with an α-halogen compound of the general Formula III

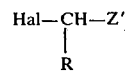

wherein R has the values given above, Z' is an amide, nitrile or alkoxycarbonyl group, and Hal is a halogen atom, preferably chlorine or bromine, and optionally thereafter hydrolyzing an acid derivative to the free acid (I, Z = COOH) and optionally converting the free acid into a physiologically acceptable salt thereof.

The reaction is conducted in a suitable solvent, preferably acetone or dimethylformamide, at a temperature of from 0° to 100° C., preferably at room temperature, in the presence of a basic catalyst, e.g., sodium carbonate, sodium hydroxide, potassium hydroxide, but preferably in the presence of potassium carbonate.

The free acid is produced in a conventional manner from the acid derivative. It is especially advantageous to hydrolyze an ester by heating to 100° C. in dioxane/sodium hydroxide solution and/or in analogous mixtures, e.g., methanol/potassium hydroxide solution, to the alkali salt of the carboxylic acid, from which the free acid is obtained by treatment with a mineral acid or strong organic acid, e.g., acetic acid.

The starting materials are either known from the literature [*J. Heterocycl. Chem.* 8, 999 (1971)], or they can be produced according to methods analogous thereto.

The compounds of this invention possess valuable pharmacological properties. Thus, with good compatibility, they exhibit antiphlogistic and antipyretic activity.

The compounds of this invention are useful, for example, for the production of analgetically active drugs in conjunction with the auxiliary substances known and customery in galenic pharmacy. They can be administered in the same manner as the known phenylbutazone.

The compounds of this invention can be employed in admixture with conventional excipients, i.e., pharmaceutically acceptable liquid, semi-liquid or solid organic or inorganic carriers suitable, e.g., for parenteral or enteral application and which do not deleteriously react with the active compound in admixture therewith. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are unit dosage forms, e.g., tablets, dragees or capsules having talc and/or a carbohydrate carrier or binder or the like, the carrier preferably being lactose and/or corn starch and/or potato starch; particulate solids, e.g., granules, and liquids and semi-liquids, e.g., syrups and elixirs or the like, wherein a sweetened vehicle is employed. Sustained release compositions can be formulated including those wherein the active compound is protected with differentially degradable coatings, e.g., by microencapsulation, multiple coatings, etc.

Suitable for oral administration are, inter alia, tablets, dragees, capsules, pills, granules, suspensions and solutions. Each unit dose, e.g., each tablespoon of liquid or each tablet, contains for example, 10–500 mg. of the effective agent.

Solutions for parenteral application contain, for example, 0.01–5 % of effective agent in an aqueous solution.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

Methyl Ester of (1,4-Diphenyl-3-pyrazolyloxy)-acetic Acid 2.6 g. (24 millimoles) of the methyl ester of chloroacetic acid is added all at once to a suspension of 4.73 g. (20 millimoles) of 3-hydroxy-1,4-diphenylpyrazole (m.p. 202°–204° C.) and 5.54 g. (40 millimoles) of potassium carbonate in 30 ml. of dry dimethylformamide; the mixture is agitated overnight at room temperature. After filtration, the DMF phase is concentrated and the resultant oil taken up in 100 ml. of chloroform. The chloroform phase is washed three times with respectively 50 ml. of water, dried over sodium sulfate, and concentrated. The thus-separated crude product is pressed out on clay and recrystallized from n-propanol with the addition to active carbon; m.p. 99°–100° C. Yield: 3.38 g. (55% of theory).

EXAMPLE 2

(1,4-Diphenyl-3-pyrazolyloxy)-acetic Acid 3.90 g. (12.5 mmol) Of the methyl ester of (1,4-diphenyl-3-pyrazolyloxy)-acetic acid is heated for 45 minutes on a steam bath in a mixture of 15 ml. of 1N NaOH and 25 ml. of dioxane. The mixture is adjusted, after cooling, to pH 7.0 with 4N HCl, then concentrated to oily consistency, taken up in 150 ml. of chloroform, and filtered. The thus-obtained solution is washed twice with respectively 50 ml. of water, dried over sodium sulfate, and concentrated. The crystalline residue has a melting point of 172° C. which does not rise after recrystallization from chloroform/petroleum ether. Yield: 3.42 g. (92% of theory).

EXAMPLE 3

Methyl Ester of [1-(p-Chlorophenyl)-4-phenyl-3-pyrazolyloxy]-acetic Acid

The compound is prepared analogously to Example 1 from 3-hydroxy-1-(p-chlorophenyl)-4-phenylpyrazole (m.p. 250°–252° C.) and methyl chloroacetate. M.p. 105°–106° C. (from propanol). Yield: 65% of theory.

EXAMPLE 4

[1-(p-Chlorophenyl)-4-phenyl-3-pyrazolyloxy]-acetic Acid

The compound is produced analogously to Example 2 from the methyl ester of [1-(p-chlorophenyl)-4-phenyl-3-pyrazolyloxy]-acetic acid; m.p. 149°–150° C. (water/propanol). Yield: 81% of theory.

EXAMPLE 5

Methyl Ester of [1-Phenyl-4-(p-chlorophenyl)-3-pyrazolyloxy]-acetic Acid

This compound is prepared analogously to Example 1 from 3-hydroxy-1-phenyl-4-(p-chlorophenyl)-pyrazole (m.p. 248°–249° C.) and methyl chloroacetate; m.p. 139°–140° C. (n-propanol). Yield: 67% of theory.

EXAMPLE 6

[1-Phenyl-4-(p-chlorophenyl)-3-pyrazolyloxy]-acetic Acid

This substance is prepared analogously to Example 2 from the methyl ester of [1-phenyl-4-(p-chlorophenyl)-3-pyrazolyloxy]-acetic acid; m.p. 174° C. (n-propanol/water). Yield: 60% of theory.

By reacting the acid with equimolar amounts of methylglucamine in an ethanolic solution, the crystalline methylglucamine salt is obtained; m.p. 144°–147° C. Yield: 91% of theory.

EXAMPLE 7

Methyl Ester of [1,4-Di-(p-chlorophenyl)-3-pyrazolyloxy]-acetic Acid

This compound is prepared in analogy to Example 1 from 3-hydroxy-1,4-di-(p-chlorophenyl)-pyrazole (m.p. 294°–295° C.) and methyl chloroacetate; m.p. 162°–163° C. (propanol). Yield: 40% theory.

EXAMPLE 8

[1,4-Di-(p-chlorophenyl)-3-pyrazolyloxy]-acetic Acid

The compound is produced analogously to Example 2 from the methyl ester of [1,4-di-(p-chlorophenyl)-3-pyrazolyloxy]-acetic acid; m.p. 183°–184° C. (propanol/water). Yield: 73% of theory.

EXAMPLE 9

Butyl Ester of [1-(p-Methoxyphenyl)-4-phenyl-3-pyrazolyloxy]-acetic Acid

The compound is prepared analogously to Example 1 from 3-hydroxy-1-(p-methoxyphenyl)-4-phenyl-pyrazole and butyl chloroacetate.

EXAMPLE 10

[1-(p-Methoxyphenyl)-4-phenyl-3-pyrazolyloxy]-acetic Acid

This compound is produced analogously to Example 2 from the butyl ester of [1-(p-methoxyphenyl)-4-phenyl-3-pyrazolyloxy]-acetic acid.

EXAMPLE 11

Methyl Ester of [1-Phenyl-4-(p-methoxyphenyl)-3-pyrazolyloxy]-acetic Acid

This compound is prepared in analogy to Example 1 from 3-hydroxy-1-phenyl-4-(p-methoxyphenyl)-pyrazole (m.p. 194°–195° C.) and methyl chloroacetate; m.p. 113°–114° C. (propanol). Yield: 48% theory.

EXAMPLE 12

[1-Phenyl-4-(p-methoxyphenyl)-3-pyrazolyloxy]-acetic Acid

The compound is produced analogously to Example 2 from the methyl ester of [1-phenyl-4-(p-methoxyphenyl)-3-pyrazolyl]-acetic acid; m.p. 173°–174° C. (propanol/water). Yield: 69% of theory.

EXAMPLE 13

Methyl Ester of [1-(o-Methoxyphenyl)-4-phenyl-3-pyrazolyloxy]-acetic Acid

This compound is prepared in analogy to Example 1 from 3-hydroxy-1-(o-methoxyphenyl)-4-phenyl-pyrazole (m.p. 187°–188° C.) and methyl chloroacetate. Yield: 47% of theory.

EXAMPLE 14

[1-(o-Methoxyphenyl)-4-phenyl-3-pyrazolyloxy]-acetic Acid

The compound is prepared analogously to Example 2 from the methyl ester of [1-(o-methoxyphenyl)-4-phenyl-3-pyrazolyloxy]-acetic acid; m.p. 170°–174° C. (propanol). Yield: 33% of theory.

EXAMPLE 15

Methyl Ester of [1-Phenyl-4-(o-methoxyphenyl)-3-pyrazolyloxy]-acetic Acid

This compound is produced analogously to Example 1 from 3-hydroxy-1-phenyl-4-(o-methoxyphenyl)-pyrazole (m.p. 165°–167° C.) and methyl chloroacetate; m.p. 87°–90° C. (isopropanol). Yield: 55% of theory.

EXAMPLE 16

[1-Phenyl-4-(o-methoxyphenyl)-3-pyrazolyloxy]-acetic Acid

This substance is produced in analogy to Example 2 from the methyl ester of [1-phenyl-4-(o-methoxyphenyl)-3-pyrazolyloxy]-acetic acid; m.p. 160°–161° C. (ethanol). Yield: 26% of theory.

EXAMPLE 17

Methyl Ester of [1-Phenyl-4-(o-methylphenyl)-3-pyrazolyloxy]-acetic Acid

The substance is prepared analogously to Example 1 from 3-hydroxy-1-phenyl-4-(o-methylphenyl)-pyrazole (m.p. 164°–170° C.) and methyl chloroacetate. Yield: 45% of theory.

EXAMPLE 18

[1-Phenyl-4-(o-methylphenyl)-3-pyrazolyloxy]-acetic Acid

This compound is prepared in analogy to Example 2 from the methyl ester of [1-phenyl-4-(o-methylphenyl)-3-pyrazolyloxy]-acetic acid. The acid, pure as determined by thin-layer chromatography, is a colorless oil which does not crystallize. Yield: 10% of theory.

EXAMPLE 19

Methyl Ester of [1-(o-Methylphenyl)-4-phenyl-3-pyrazolyloxy]-acetic Acid

This substance is prepared analogously to Example 1 from 3-hydroxy-1-(o-methylphenyl)-4-phenylpyrazole (m.p. 141°–143° C.) and methyl chloroacetate. Yield: 49% theory.

EXAMPLE 20

[1-(o-Methylphenyl)-4-phenyl-3-pyrazolyloxy]-acetic Acid

This compound is produced in analogy to Example 2 from the methyl ester of [1-(o-methylphenyl)-4-phenyl-3-pyrazolyloxy]-acetic acid. The pure acid obtained after chromatography on silica gel (eluent: hexane/acetone/formic acid = 84:15:1) is an oil which does not crystallize. Yield: 12% of theory.

EXAMPLE 21

Methyl Ester of [1-(3,4-Dichlorophenyl)-4-phenyl-3-pyrazolyloxy]-acetic Acid

This substance is produced analogously to Example 1 from 3-hydroxy-1-(3,4-dichlorophenyl)-4-phenyl-pyrazole (m.p. 244°–245° C.) and methyl chloroacetate; m.p. 108°–115° C. (n-propanol/water). Yield: 27% of theory.

EXAMPLE 22

[1-(3,4-Dichlorophenyl)-4-phenyl-3-pyrazolyloxy]-acetic Acid

The compound is prepared analogously to Example 2 from the methyl ester of [1-(3,4-dichlorophenyl)-4-phenyl-3-pyrazolyloxy]-acetic acid. Yield: 49% of theory.

EXAMPLE 23

Methyl Ester of [1-Phenyl-4-(3,4-dichlorophenyl)-3-pyrazolyloxy]-acetic Acid

This compound is prepared in analogy to Example 1 from 3-hydroxy-1-phenyl-4-(3,4-dichlorophenyl)-pyrazole (m.p. 274°–275° C.) and methyl chloroacetate; m.p. 148° C. (propanol). Yield: 67% of theory.

EXAMPLE 24

[1-Phenyl-4-(3,4-dichlorophenyl)-3-pyrazolyloxy]-acetic Acid

This compound is produced analogously to Example 2 from the methyl ester of [1-phenyl-4-(3,4-dichlorophenyl)-3-pyrazolyloxy]-acetic acide; m.p. 218°–220° C. (propanol/water). Yield: 71% of theory.

EXAMPLE 25

Methyl Ester of [1-(Benzyl)-4-phenyl-3-pyrazolyloxy]-acetic Acid

This compound is prepared analogously to Example 1 from 3-hydroxy-1-(benzyl)-4-phenylpyrazole (m.p. 226°–228° C.) and methyl chloroacetate; m.p. 73°–74° C. (n-propanol). Yield: 52% of theory.

EXAMPLE 26

[1-(Benzyl)-4-phenyl-3-pyrazolyloxy]-acetic Acid

This compound is prepared in analogy to Example 2 from the methyl ester of [1-(benzyl-4-phenyl-3-pyrazolyloxy]-acetic acid; m.p. 132°–133° C. (n-propanol/H$_2$O). Yield: 72% of theory.

EXAMPLE 27

Methyl Ester of [1-Phenyl-4-(benzyl)-3-pyrazolyloxy]-acetic Acid

This compound is produced analogously to Example 1 from 3-hydroxy-1-phenyl-4-(benzyl)-pyrazole (m.p. 185°–186° C.) and methyl chloroacetate. Yield: 52% of theory.

EXAMPLE 28

[1-Phenyl-4-(benzyl)-3-pyrazolyloxy]-acetic Acid

This substance is produced in analogy to Example 2 from the methyl ester of [1-phenyl-4-(benzyl)-3-pyrazolyloxy]-acetic acid; m.p. 130°–131° C. (ethanol/water). Yield: 41% of theory.

EXAMPLE 29

Methyl Ester of [1-(2,4-Dimethylphenyl)-4-phenyl-3-pyrazolyloxy]-acetic Acid

This compound is prepared analogously to Example 1 from 3-hydroxy-1-(2,4-dimethylphenyl)-4-phenyl-pyrazole and methyl chloroacetate. Yield: 37% of theory.

EXAMPLE 30

[1-(2,4-Dimethylphenyl)-4-phenyl-3-pyrazolyloxy]-acetic Acid

This substance is prepared in analogy to Example 2 from the methyl ester of [1-(2,4-dimethylphenyl)-4-phenyl-3-pyrazolyloxy]-acetic acid. Yield: 57% of theory.

EXAMPLE 31

Ethyl Ester of (1,4-Diphenyl-3-pyrazolyloxy)-α-methylacetic Acid

This compound is prepared analogously to Example 1 from 3-hydroxy-1,4-diphenylpyrazole with ethyl α-bromopropionate. Yield: 91% of theory.

EXAMPLE 32

(1,4-Diphenyl-3-pyrazolyloxy)-α-methylacetic Acid

This compound is prepared analogously to Example 2 from the ethyl ester of (1,4-diphenyl-3-pyrazolyloxy)-2-propionic acid; m.p. 175°–178° C. (ethanol/H$_2$O). Yield: 40% of theory.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

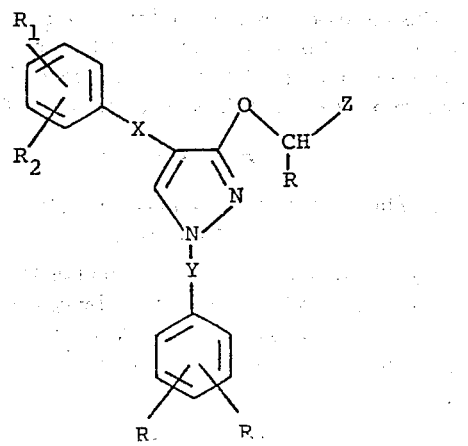

wherein R is a hydrogen atom or alkyl of 1–4 carbon atoms; $R_1$, $R_2$, $R_3$ and $R_4$ each are a hydrogen atom, a halogen atom, alkyl of 1–4 carbon atoms or alkoxy of 1–4 carbon atoms; X and Y each are a bond joining the benzene ring to the pyrazole ring or methylene; and Z is a carboxyl or alkoxycarbonyl of 1–6 carbon atoms in the alkoxy group, and when Z is carboxyl physiologically acceptable, salts thereof with physiologically acceptable base.

2. A compound of claim 1 wherein Z is carboxyl or alkoxycarbonyl of 1–6 carbon atoms in the alkoxy group.

3. A compound of claim 2 wherein R is a hydrogen atom.

4. A compound of claim 3 wherein X and Y each are bonds.

5. A compound of claim 4 wherein $R_1$, $R_2$, $R_3$ and $R_4$ each are hydrogen atoms, Cl, $CH_3$ or $OCH_3$.

6. A compound of claim 5 wherein $R_1$ and $R_2$ or $R_3$ and $R_4$ are hydrogen atoms.

7. A compound of claim 1, methyl ester of (1,4-diphenyl-3-pyrazolyloxy)-acetic acid.

8. A compound of claim 1, (1,4-diphenyl-3-pyrazolyloxy)-acetic acid.

9. A compound of claim 1, methyl ester of [1-(p-chlorophenyl)-4-phenyl-3-pyrazolyloxy]-acetic acid.

10. A compound of claim 1, [1-(p-chlorophenyl)-4-phenyl-3-pyrazolyloxy]-acetic acid.

11. A compound of claim 1, methyl ester of [1-phenyl-4-(p-chlorophenyl)-3-pyrazolyloxy]-acetic acid.

12. A compound of claim 1, [1-phenyl-4-(p-chlorophenyl)-3-pyrazolyloxy]-acetic acid.

13. A compound of claim 1, methylglucamine salt of [1-phenyl-4-(p-chlorophenyl)-3-pyrazolyloxy]-acetic acid.

14. A compound of claim 1, methyl ester of [1,4-di(p-chlorophenyl)-3-pyrazolyloxy]-acetic acid.

15. A compound of claim 1, [1,4-di(p-chlorophenyl)-3-pyrazolyloxy]-acetic acid.

16. A compound of claim 1, butyl ester of [1-p-methoxyphenyl)-4-phenyl-3-pyrazolyloxy]-acetic acid.

17. A compound of claim 1, [1-(p-methoxyphenyl)-4-phenyl-3-pyrazolyloxy]-acetic acid.

18. A compound of claim 1, methyl ester of [1-phenyl-4-(p-methoxyphenyl-3-pyrazolyloxy]-acetic acid.

19. A compound of claim 1, [1-phenyl-4-(p-methoxyphenyl-3-pyrazolyloxy]-acetic acid.

20. A compound of claim 1, methyl ester of [1-(o-methoxyphenyl)-4-phenyl-3-pyrazolyloxy]-acetic acid.

21. A compound of claim 1, [1-(o-methoxyphenyl)-4-phenyl-3-pyrazolyloxy]-acetic acid.

22. A compound of claim 1, methyl ester of [1-phenyl-4-(o-methoxyphenyl)-3-pyrazolyloxy]-acetic acid.

23. A compound of claim 1, [1-phenyl-4-(o-methoxyphenyl)-3-pyrazolyloxy]-acetic acid.

24. A compound of claim 1, methyl ester of [1-phenyl-4-(o-methylphenyl)-3-pyrazolyloxy]-acetic acid.

25. A compound of claim 1, [1-phenyl-4-(o-methylphenyl)-3-pyrazolyl]-acetic acid 26. A compound of claim 1, methyl ester of [1-(o-methylphenyl)-4-phenyl-3-pyrazolyloxyl]-acetic acid.

27. A compound of claim 1, [1-(o-methylphenyl)-4-phenyl-3-pyrazolyloxy]-acetic acid.

28. A compound of claim 1, methyl ester of [1-(3,4-dichlorophenyl)-4-phenyl-3-pyrazolyloxy]-acetic acid.

29. A compound of claim 1, [ 1-(3,4-dichlorophenyl)-4-phenyl-3-pyrazolyloxy]-acetic acid.

30. A compound of claim 1, methyl ester of [1-phenyl-4-(3,4-dichlorophenyl)-3-pyrazolyloxy]-acetic acid.

31. A compound of claim 1, [1-phenyl-4-(3,4-dichlorophenyl)-3-pyrazolyloxy]-acetic acid.

32. A compound of claim 1, methyl ester of (1-benzyl-4-phenyl-3-pyrazolyloxy)-acetic acid.

33. A compound of claim 1, (1-benzyl-4-phenyl-3-pyrazolyloxy)-acetic acid.

34. A compound of claim 1, methyl ester of [1-phenyl-4-benzyl-3-pyrazolyloxy)-acetic acid.

35. A compound of claim 1, (1-phenyl-4-benzyl-3-pyrazolyloxy)-acetic acid.

36. A compound of claim 1, methyl ester of [1-(2,4-dimethylphenyl)-4-phenyl-3-pyrazolyloxy]-acetic acid.

37. A compound of claim 1, [1-(2,4-dimethylphenyl)-4-phenyl-3-pyrazolyl]-acetic acid.

38. A compound of claim 1, ethyl ester of (1,4-diphenyl-3-pyrazolyloxy)-α-methylacetic acid.

39. A compound of claim 1, (1,4-diphenyl-3-pyrazolyloxy)-α-methylacetic acid.

40. A pharmaceutical composition in unit dosage form comprising an anti-inflammatory or antipyretic effective amount of compound of claim 1 in admixture with a pharmaceutically acceptable carrier.

* * * * *